United States Patent
Chen et al.

(10) Patent No.: US 9,056,153 B2
(45) Date of Patent: Jun. 16, 2015

(54) BIOCOMPATIBLE POLYMERS FOR COATING OR FABRICATING IMPLANTABLE MEDICAL DEVICES

(75) Inventors: Mingfei Chen, Santa Rosa, CA (US); Peiwen Cheng, Santa Rosa, CA (US); Kishore Udipi, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 598 days.

(21) Appl. No.: 12/414,858

(22) Filed: Mar. 31, 2009

(65) Prior Publication Data

US 2010/0247597 A1 Sep. 30, 2010

(51) Int. Cl.
| | |
|---|---|
| C08F 220/26 | (2006.01) |
| A61F 2/04 | (2013.01) |
| A61K 31/436 | (2006.01) |
| A61F 2/06 | (2013.01) |
| A61L 31/04 | (2006.01) |
| A61L 27/16 | (2006.01) |
| A61L 27/34 | (2006.01) |
| A61L 31/10 | (2006.01) |

(52) U.S. Cl.
CPC ............... *A61L 31/048* (2013.01); *A61L 27/16* (2013.01); *A61L 27/34* (2013.01); *A61L 31/10* (2013.01)

(58) Field of Classification Search
None
See application file for complete search history.

(56) References Cited

U.S. PATENT DOCUMENTS

| | | | |
|---|---|---|---|
| 6,143,322 A | 11/2000 | Sackler et al. | |
| 6,286,955 B1 | 9/2001 | Akashi | |
| 6,530,950 B1 | 3/2003 | Alvarado et al. | |
| 6,653,426 B2 | 11/2003 | Alvarado et al. | |
| 2002/0065551 A1 | 5/2002 | Koole | |
| 2007/0244284 A1* | 10/2007 | Cheng et al. | 526/319 |

FOREIGN PATENT DOCUMENTS

| | | |
|---|---|---|
| GB | 1 411 577 A | 10/1975 |
| JP | 50024588 | 3/1975 |
| WO | WO 98/29145 | 7/1998 |
| WO | WO2009/111021 A1 | 9/2009 |

OTHER PUBLICATIONS

Bar et al. "New biocompatible polymer surface coating for stents results in a low neointimal response", J Biomed Mater Res, (2000), 52(1), pp. 193-198.*
Jones et al. "Characterization of the physiochemical antimicobial and drug release properties of thermoresponsive hydrogel copolyers designed for medical device applicaitons", J Biomed Mat Res B, (2007), 85B (2), pp. 417-424.*
Jones et al. "Characterization of the physiochemical antimicrobial and drug release properties of thermoresponsive hydrogel copolymers designed for medical device applications" J Biomed Mat Res B, 2007, 85B(2), pp. 417-424.*
Int'l Search Report for Int'l App. No. PCT/US2010/027598, Mar. 17, 2010, Medtronic Vascular Inc.
Hezi-Yamit et al. "Novel High Throughput Polymer Biocompatibility Screening Designed for SAR (Structure-Activity Relationship): Application for Evaluating Polymer Coatings for Cardiovascular Drug-Eluting Stents" Combinatorial Chemistry & High Throughput Screenings, 2009, 12, 664-676.

* cited by examiner

*Primary Examiner* — Kortney L Klinkel
*Assistant Examiner* — Melissa Javier

(57) ABSTRACT

The present disclosure generally relates to biocompatible polymers for coating or fabricating implantable medical devices and to implantable medical devices having the present biocompatible polymers. The disclosed biocompatible polymers exhibit superior biocompatibility and therefore minimize unwanted immune reaction from a patient into whom a medical device is implanted.

6 Claims, No Drawings

BIOCOMPATIBLE POLYMERS FOR COATING OR FABRICATING IMPLANTABLE MEDICAL DEVICES

FIELD OF THE INVENTION

The present disclosure generally relates to biocompatible polymers useful for coating or fabricating implantable medical devices.

BACKGROUND OF THE INVENTION

Cardiovascular disease, specifically atherosclerosis, remains a leading cause of death in developed countries. Atherosclerosis is a multifactorial disease that results in a narrowing, or stenosis, of a vessel lumen. Briefly, pathologic inflammatory responses resulting from vascular endothelium injury includes the expression of chemokines and adhesion molecules leading to the migration of monocytes and vascular smooth muscle cells (VSMC) from the sub endothelium into the arterial wall's intimal layer. There the VSMC proliferate and lay down an extracellular matrix causing vascular wall thickening and reduced vessel patency.

Cardiovascular disease caused by stenotic coronary arteries is commonly treated using either coronary artery by-pass graft (CABG) surgery or angioplasty. Angioplasty is a percutaneous procedure wherein a balloon catheter is inserted into the coronary artery and advanced until the vascular stenosis is reached. The balloon is then inflated restoring arterial patency. One angioplasty variation includes arterial stent deployment. Briefly, after arterial patency has been restored, the balloon is deflated and a vascular stent is inserted into the vessel lumen at the stenosis site. After expansion of the stent, the catheter is then removed from the coronary artery and the deployed stent remains implanted to prevent the newly opened artery from constricting spontaneously. An alternative procedure involves stent deployment without prior balloon angioplasty, the expansion of the stent against the arterial wall being sufficient to open the artery, restoring arterial patency. However, balloon catheterization and/or stent deployment can result in vascular injury ultimately leading to VSMC proliferation and neointimal formation within the previously opened artery. This biological process whereby a previously opened artery becomes re-occluded is referred to as restenosis.

Implantable medical devices have become increasingly more common over the last fifty years and have found applications in nearly every branch of medicine. Examples include joint replacements, vascular grafts, heart valves, ocular lenses, pacemakers, vascular stents, urethral stents, and many others. However, regardless of the application, implantable medical devices must be biocompatible. They must be fabricated from materials that will not elicit an adverse biological response such as, but not limited to, inflammation, thrombogensis or necrosis. Thus, early medical devices were generally fabricated from inert materials such as precious metals and ceramics. More recently, stainless steel and other metal alloys have replaced precious metals and polymers are being substituted for ceramics.

Stents and/or drug therapies, either alone or in combination with the PTCA procedure, are often used to avoid or mitigate the effects or occurrence of restenosis. In general, stents are mechanical scaffoldings which may be inserted into a blocked or narrowed region of a passageway to provide and maintain its patency. During implantation, a stent can be positioned on a delivery device (for example and without limitation a balloon catheter) and advanced from an external location to an area of passageway blockage or narrowing within the body of the patient. Once positioned, the delivery device can be actuated to deploy the radially expandable stent. Expansion of the stent can result in the application of force against the internal wall of the passageway, thereby improving the patency of the passageway. Thereafter, the delivery device can be removed from the patient's body.

Stents may be manufactured in a variety of lengths and diameters and from a variety of materials ranging from metallic materials to polymers. Stents may also incorporate and release drugs (i.e., "drug-eluting stents") that can affect endothelialization as well as the formation of and treatment of existing plaque and/or blood clots. In some instances then, drug-eluting stents can reduce, or in some cases, eliminate, the incidence of endothelialization, thrombosis and/or restenosis.

Additionally, recent advances in in situ drug delivery has led to the development of implantable medical devices specifically designed to provide therapeutic compositions to remote anatomical locations. Perhaps one of the most exciting areas of in situ drug delivery is in the field of intervention cardiology. Vascular occlusions leading to ischemic heart disease are frequently treated using percutaneous transluminal coronary angioplasty (PTCA) whereby a dilation catheter is inserted through a femoral artery incision and directed to the site of the vascular occlusion. The catheter is dilated and the expanding catheter tip (the balloon) opens the occluded artery restoring vascular patency. Generally, a vascular stent is deployed at the treatment site to minimize vascular recoil and restenosis. However, in some cases stent deployment leads to damage to the intimal lining of the artery which may result in vascular smooth muscle cell hyperproliferation and restenosis. When restenosis occurs it is necessary to either re-dilate the artery at the treatment site, or, if that is not possible, a surgical coronary artery bypass procedure must be performed.

Recently, it has been determined that drug-eluting stents coated with anti-proliferative drugs such as, but not limited to, rapamycin and its analogs and paclitaxel have shown great promises in preventing restenosis. However, there is a need to develop additional and potentially more efficacious drug-eluting stents (DES). One critical factor in DES efficacy is the drug elution rate. Drug elution is generally a factor of the drug's solubility in the polymer coating applied to the stent.

One of the critical components of a drug eluting stent is the polymer coating material. The coating material serves as the reservoir from which drug release is controlled. After all of the drug has bee released or depleted, the polymeric coating may serve as a permanent implant material. For the success of a permanent implant, the must be biocompatible. The polymer coating is a foreign material to the body of a patient. It may cause an unwanted immune reaction from the body and result in implant rejection. Thus, there continues to be a need for improving biocompatibility for polymer materials which are used to fashion or coat implantable medical devices.

SUMMARY OF THE INVENTION

The normal host response to an implant includes trauma, inflammation, the immune system's reaction, and eventual healing and scarring. Biomaterials exhibiting a lack of biocompatibility could induce many complications which might include long-lasting chronic inflammation or cytotoxic chemical buid-up. It is the object of the present disclosure to provide biocompatible polymeric materials exhibiting improved biocompatibility.

Biocompatibility is the property of not incurring a toxic or detrimental immunological response. More specifically, as used herein "biocompatible" shall mean any material that does not cause injury or death to the animal or induce an adverse reaction in an animal when placed in intimate contact with the animal's tissues. Adverse reactions include inflammation, infection, fibrotic tissue formation, cell death, or thrombosis.

Therefore, in one embodiment, the present disclosure relates to a biocompatible polymer for coating or fabricating an implantable medical device comprising: a first monomer and a second monomer wherein said first monomer is a hydroxyalkyl methacrylate and said second monomer is an acrylate monomer. In another embodiment of the biocompatible polymer for coating or fabricating an implantable medical device, the first monomer is 4-hydroxybutyl methacrylate. In another embodiment of the biocompatible polymer for coating or fabricating an implantable medical device, the first monomer is 4-hydroxybutyl methacrylate. In another embodiment of the biocompatible polymer for coating or fabricating an implantable medical device, the second monomer is an acrylate monomer selected from the group consisting of hexyl methacrylate, butyl methacrylate, ethyl methacrylate, lauryl methacrylate, hydroxypropyl methacrylate, and 2-hydroxyethyl methacrylate. In another embodiment of the biocompatible polymer for coating or fabricating an implantable medical device, the second monomer is methyl methacrylate. In another embodiment of the biocompatible polymer for coating or fabricating an implantable medical device, the second monomer is hexyl methacrylate. In another embodiment of the biocompatible polymer for coating or fabricating an implantable medical device, the second monomer is butyl methacrylate.

The present disclosure also relates to an implantable medical device comprising: a biocompatible polymer comprising a first monomer and a second monomer wherein the first monomer is a hydroxyalkyl methacrylate and the second monomer is an acrylate monomer. In another embodiment of the implantable medical device, the first monomer is 4-hydroxybutyl methacrylate. In another embodiment of the implantable medical device, the first monomer is 2-hydroxyethyl methacrylate. In another embodiment of the implantable medical device, the second monomer is an acrylate monomer selected from the group consisting of hexyl methacrylate, butyl methacrylate, ethyl methacrylate, lauryl methacrylate, hydroxypropyl methacrylate, and 2-hydroxyethyl methacrylate. In another embodiment of the implantable medical device, the second monomer is methyl methacrylate. In another embodiment of the implantable medical device, the second monomer is hexyl methacrylate. In another embodiment of the implantable medical device, the second monomer is butyl methacrylate. In another embodiment of the implantable medical device, the second monomer is ethyl methacrylate. In another embodiment of the implantable medical device, the biocompatible coating further comprises a bioactive agent selected from the group consisting of antiproliferatives, estrogens, chaperone inhibitors, protease inhibitors, protein-tyrosine kinase inhibitors, leptomycin B, peroxisome proliferator-activated receptor gamma ligands (PPAR γ), hypothemycin, nitric oxide, bisphosphonates, epidermal growth factor inhibitors, antibodies, proteasome inhibitors, antibiotics, anti-sense nucleotides, and transforming nucleic acids. In another embodiment of the implantable medical device, the anti-proliferative is zotarolimus. In another embodiment of the implantable medical device, the implantable medical device is a vascular stent.

The present disclosure also relates to a vascular stent comprising: a biocompatible polymer comprising a first monomer and a second monomer wherein said first monomer is a 4-hydroxybutyl methacrylate or 2-hydroxyethyl methacrylate and said second monomer is hexylmethacrylate or n-hexylmethacrylate.

DETAILED DESCRIPTION OF THE INVENTION

Cardiovascular disease is the leading cause of death in the United States. A significant portion of these deaths are caused by coronary artery disease, the clogging of arteries due to cholesterol buildup. A method for combating this vessel blockage is balloon angioplasty coupled with stenting. Using a catheter guidewire, surgeons insert a balloon into a blocked vessel. This balloon is attached to a stent. The balloon expands, pushing away cholesterol, while leaving the stent in place. This expandable mesh cylinder then supports the damaged blood vessel after the balloon and guidewire are withdrawn. In general, to provide effective treatment for coronary artery disease, the material creating the stent must be flexible, supportive, capable of expansion, and biocompatible. Biocompatibility is the property of not incurring a toxic or detrimental immunological response. The normal host response to an implant includes trauma, inflammation, the immune system's reaction, and eventual healing or scarring. Biomaterials exhibiting a lack of biocompatibility could induce many complications, which might include long-lasting chronic inflammation or cytotoxic chemical buildup. To avoid these potential difficulties, scientists must test for the biocompatibility of substances, first in vitro and then in vivo. A few of the medical complications arising from coronary stents today include thrombosis, cholesterol accumulation, restenosis, inflammation, and hyperplasia. Thrombosis is the formation of a clot, or the presence of a blood clot within a blood vessel. Cholesterol, which accumulates from saturated fat buildup within the blood vessels, can reform its original plaques atop the inserted stents. Restenosis is the re-closing or the collapsing of an artery. Inflammation might be caused by the body's immune response, warding off the invasive material.

Hyperplasia is an abnormal increase in the number of cells in the surrounding tissue. Presently, most stents consist of a stainless steel framework. However, this 316L steel is not fully biocompatible, and has induced high occurrences of restenosis and thrombosis. Scientists are therefore researching more biocompatible options, which include gold, titanium, cobalt-chromium alloys, tantalum alloys, nitinol, and various polymers.

Materials that are not biocompatible induce many complications in the body. Chemical or physical properties can cause prolonged chronic inflammation, resulting in local cell damage. Movement between the implant and the tissue would disrupt cells at any point of contact. As the body wears down plastics, small particles can cause irritation and also clog macrophage lysosomes. If the white blood cells cannot break down these particles, the particles will remain within the cells.

Stainless steel, the most common inexpensive stent material in use today has much room for improvement regarding biocompatibility. The current metal options available seem to incur high restenosis and thrombosis rates, and a need for repeat revascularization. Polymer materials in use today also have much room for increasing biocompatibility.

Therefore the present disclosure relates to a biocompatible polymer for coating or fabricating an implantable medical device comprising: a first monomer and a second monomer wherein the first monomer is a hydroxyalkyl methacrylate and the second monomer is an acrylate monomer.

The present biocompatible polymeric coatings comprise polymers having at least two monomers. A polymer is a large molecule (macromolecule) composed of repeating structural units typically connected by covalent chemical bonds. Monomer is a small molecule that can become chemically bonded to other monomers to form a polymer. As used herein a "copolymer" will be defined as a macromolecule produced by the simultaneous or step-wise polymerization of two or more dissimilar units such as monomers. Copolymer shall include biopolymers (two dissimilar unit), terpolymer (three dissimilar units), etc. Because the first monomer is hydroxyalkyl methacrylate and the second monomer is an acrylate monomer in one embodiment, the biocompatible polymeric coatings are made of copolymers.

By varying the amount of monomers used as well the reaction conditions the properties of the polymers can be fine tuned for drug delivery, mores specifically controlled drug release rates. The biocompatible polymers of the present disclosure are suitable for the controlled release of both hydrophobic and hydrophilic drugs, either independently or in combination. As used herein in reference to the bioactive agent or drugs, "hydrophilic" refers to a bioactive agent that has a solubility in water of more than 200 micrograms per milliliter. As used herein in reference to the bioactive agent or drug the term "hydrophobic" refers to a bioactive agent that has a solubility in water of no more than 200 micrograms per milliliter.

As used herein "controlled release" refers to the release of a bioactive compound from a medical device surface at a predetermined rate. Controlled release implies that the bioactive compound does not come off the medical device surface sporadically in an unpredictable fashion and does not "burst" off of the device upon contact with a biological environment (also referred to herein a first order kinetics) unless specifically intended to do so. However, the term "controlled release" as used herein does not preclude a "burst phenomenon" associated with deployment. In some embodiments of the present invention an initial burst of drug may be desirable followed by a more gradual release thereafter. The release rate may be steady state (commonly referred to as "timed release" or zero order kinetics), that is the drug is release in even amounts over a predetermined time (with or without an initial burst phase) or may be a gradient release. A gradient release implies that the concentration of drug released from the device surface changes over time.

Controlling drug release rates from the polymers of the present disclosure requires adjusting the properties of the polymers. One non-limiting method of controlling drug release rates in the polymers of the present disclosure involves controlling the glass transition temperature (Tg) of the polymers. As used herein, glass transition temperature (Tg) refers to a temperature wherein a polymer structurally transitions from an elastic pliable state to a rigid and brittle state.

Medical devices suitable for coating with the present biocompatible polymers of the present disclosure include, but are not limited to, vascular stents, stent grafts, urethral stents, bile duct stents, catheters, guide wires, pacemaker leads, bone screws, sutures and prosthetic heart valves. Medical devices which can be manufacture from the present biocompatible polymers include, but are not limited to, vascular stents, stent grafts, urethral stents, bile duct stents, catherters, guide wires, pacemaker leads, bone screws, sutures and prosthetic heart valves.

The present biocompatible polymers include hydroxyalkyl methacrylate as a first monomer. In one embodiment of the present biocompatible polymer for coating or fabricating an implantable medical device, first monomer is 4-hydroxybutyl methacrylate.

The structure of 4-hydroxybutyl methacrylate is represented below:

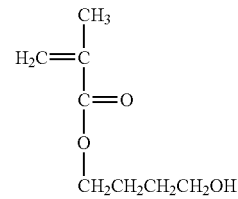

A second monomer of the present biocompatible polymers may be an acrylate monomer. In one embodiment, the second monomer is hexyl methacrylate. The structure of hexyl methacrylate is represented below:

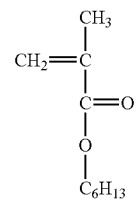

Putting the two monomers together, a copolymer is produced:

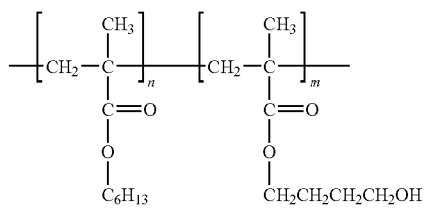

In one embodiment, n and m can be the same or different and is an integer that is greater than equal to 1 and less than or equal to 20,000.

Without being bound to any theory, the above polymer exhibits superior biocompatibility maybe due to its amphiphilic nature with combination of hydrophobic and hydrophilic groups in the chemical structure.

Methacrylates ($CH_2$=$CMeCOO^-$) are the salts or esters of methacrylic acid. Methacrylates contain methyl-vinyl groups, that is, two carbon atoms double bonded to each other, directly attached to the carbonyl carbon, and wherein the vinyl group is substituted with a non-terminal methyl group. Methacrylates are common monomers in polymer plastics, forming the acrylate polymers. Methacrylates easily form polymers because the double bonds are very reactive. In one embodiment of the present biocompatible polymers, the second monomer is an acrylate monomer selected from the group consisting of hexyl methacrylate, butyl methacrylate, ethyl methacrylate, lauryl methacrylate, hydroxypropyl methacrylate, and 2-hydroxyethyl methacrylate.

Implantable medical devices suitable for coating or being made with the present biocompatible polymers include, but are not limited to vascular stents, stent grafts, urethral stents, bile duct stents, catheters, guide wires, pacemaker leades, bone screws, sutures and prosthetic heart valves. The polymers of the present disclosure are also suitable for fabricating implantable medical devices. Medical devices which can be fabricated from the present biocompatible polymers include, but are not limited to, vascular stents, stent grafts, urethral stents, bile duct stents, catheters, guide wires, pacemaker leads, bone screws, sutures and prosthetic heart valves.

The polymer coatings of the present disclosure are intended for medical devices deployed in a hemodynamic environment and possess excellent adhesive properties. That is, the coating must be stably linked to the medical surface. Many different materials can be used to fabricate the substrate of implantable medical devices including, but not limited to, stainless steel, nitinol, aluminum, chromium, titanium, gold, cobalt, ceramics, and a wide range of synthetic polymeric and natural materials including, but not limited to, collagen, fibrin and plant fibers. All of these materials, and others, may be used with the polymeric coatings made in accordance with the teachings of the present disclosure. Furthermore, the polymers of the present disclosure may be used to fabricate an entire medical device.

There are many theories that attempt to explain or contribute to our understanding of how polymers adhere to surfaces. The most important forces include electrostatic and hydrogen bonding. However, other factors including wettability, absorption and resiliency also determine how well a polymer will adhere to different surfaces. Therefore, polymer base coats, or primers are often used in order to create a more uniform coating surface.

The polymeric coatings of the present disclosure can be applied to medical device surfaces, either primed or bare, in any manner known to those of ordinary skill in the art. Application methods compatible with the present invention include, but are not limited to, spraying, dipping, brushing, vacuum-deposition, and others. Moreover, the polymeric coatings of the present invention may be used with a cap coat. A cap coat as used herein refers to the outermost coating layer applied over another coating. A polymer coating of the present disclosure is applied over the primer coat. Then, a polymer cap coat is applied over the polymeric coating of the present disclosure. The cap coat may optionally serve as a diffusion barrier to control bioactive agent release. The cap coat may be merely a biocompatible polymer applied to the surface of the sent to protect the stent and have no effect on the bioactive agent release rates.

The biocompatible polymers of the present disclosure are also useful for the delivery and controlled release of drugs. Drugs that are suitable for release from the polymers of the present invention include, but are not limited to, anti-proliferative compounds, cytostatic compounds, toxic compounds, anti-inflammatory compounds, chemotherapeutic agents, analgesics, antibiotics, protease inhibitors, statins, nucleic acids, polypeptides, growth factors and delivery vectors including recombinant micro-organisms, liposomes, and the like.

In one embodiment of the present invention the drugs controllably released include, but are not limited to, macrolide antibiotics including FKBP-12 binding agents. Exemplary drugs of this class include sirolimus (rapamycin) (Formula 2), tacrolimus (FK506), everolimus (certican or RAD-001), temsirolimus (CCI-779 or amorphous rapamycin 42-ester with 3-hydroxy-2-(hydroxymethyl)-2-methylpropionic acid and zotarolimus. Additionally, and other rapamycin hydroxyesters may be used in combination with the polymers of the present disclosure.

EXAMPLES

Example 1

Metal Stent Cleaning Procedure

Stainless steel stents were placed a glass beaker and covered with reagent grade or better hexane. The beaker containing the hexane immersed stents was then placed into an ultrasonic water bath and treated for 15 minutes at a frequency of between approximately 25 to 50 KHz. Next the stents were removed from the hexane and the hexane was discarded. The stents were then immersed in reagent grade or better 2-propanol and vessel containing the stents and the 2-propanol was treated in an ultrasonic water bath as before. Following cleaning the stents with organic solvents, they were thoroughly washed with distilled water and thereafter immersed in 1.0 N sodium hydroxide solution and treated at in an ultrasonic water bath as before. Finally, the stents were removed from the sodium hydroxide, thoroughly rinsed in distilled water and then dried in a vacuum oven over night at 40° C. After cooling the dried stents to room temperature in a desiccated environment they were weighed their weights were recorded.

Example 2

Coating a Clean, Dried Stent Using a Drug/polymer System

In the following Example, ethanol is chosen as the solvent of choice. The bioactive agent is zotarolimus. Both the polymer and zotarolimus are freely soluble in ethanol. Persons having ordinary skill in the art of polymer chemistry can easily pair the appropriate solvent system to the polymer-drug combination and achieve optimum results with no more than routine experimentation.

250 mg of zotarolimus is carefully weighed and added to a small neck glass bottle containing 2.8 ml of ethanol. The zotarolimus-ethanol suspension is then thoroughly mixed until a clear solution is achieved.

Next 250 mg of the present biocompatible polymer is added to the zotarolimus-ethanol solution and mixed until the polymer is dissolved forming a drug/polymer solution.

The cleaned, dried stents are coated using either spraying techniques or dipped into the drug/polymer solution. The stents are coated as necessary to achieve a final coating weight of between approximately 10 µg to 1 mg. Finally, the coated stents are dried in a vacuum oven at 50° C. over night. The dried, coated stents are weighed and the weights recorded.

The concentration of drug loaded onto (into) the stents is determined based on the final coating weight. Final coating weight is calculated by subtracting the stent's pre-coating weight from the weight of the dried, coated stent.

Example 3

Coating a Clean, Dried Stent Using a Sandwich-type Coating

A cleaned, dry stent is first coated with the present biocompatible polymer followed by a coating of zotarolimus. Finally, a second coating of biocompatible polymer is provided to seal the stent thus creating a sandwich coated stent.

The Sandwich Coating Procedure:

100 mg of biocompatible polymer is added to a 50 mL Erlenmeyer containing 12.5 ml of ethanol. The flask was carefully mixed until all of the biocompatible polymer is dissolved. In a separate clean, dry Erlenmeyer flask 250 mg of zotarolimus is added to 11 mL of ethanol and mixed until dissolved.

A clean, dried stent is then sprayed with the present biocompatible polymer until a smooth confluent polymer layer was achieved. The stent was then dried in a vacuum oven at 50° C. for 30 minutes.

Next, successive layers of zotarolimus are applied to the polymer-coated stent. The stent is allowed to dry between each of the successive zotarolimus coats. After the final zotarolimus coating has dried, three successive coats of biocompatible polymer are applied to the stent followed by drying the coated stent in a vacuum oven at 50° C. over night. The dried, coated stent is weighed and its weight recorded.

The concentration of drug in the drug/polymer solution and the final amount of drug loaded onto the stent determine the final coating weight. Final coating weight is calculated by subtracting the stent's pre-coating weight from the weight of the dried, coated stent.

Example 4

Synthesis of Copolymer of 4-Hydroxybutyl Methacrylate and Hexyl Methacrylate

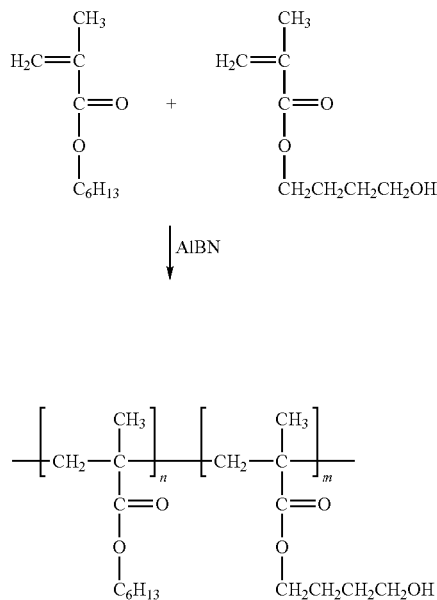

A glass bottle was charged with 1.98 g of 4-hydroxybutyl methacrylate, 6.0 g of n-hexyl methacrylate, 11.2 mL 2-butanone, 4.8 mL n-propanol and 64 mg azobisisobutyronitrile (AIBN). The bottle was sealed and purged with nitrogen gas for 30 minutes and heated in an oil bath kept at 60° C. for three hours. The polymer was purified by repeated precipitations in methanol from dichloromethane solution and dried in the oven at 45° C. overnight. An elastomeric material with a glass transition temperature of 6.5° C. was obtained.

Example 5

Synthesis of Copolymer of 2-Hydroxyethyl Methacrylate and n-Hexyl Methacrylate

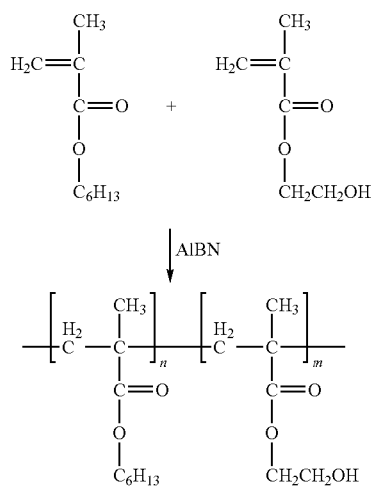

A glass bottle was charged with 2.57 g of 2-hydroxyethyl methacrylate, 2.5 g of n-hexyl methacrylate, 7 mL 2-butanone, 3 mL of n-propanol and 80 mg AIBN. The bottle was sealed and purged with nitrogen gas for 30 minutes and heated in an oil bath kept at 60° C. for five hours. The polymer was purified by repeated precipitations in methanol from dichloromethane solution and dried in the oven at 45° C. overnight. An elastomeric material with a glass transition temperature of 25° C. was obtained.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. An implantable medical device comprising:
    a biocompatible polymer comprising monomers consisting of a first monomer and a second monomer, wherein said first monomer is 2-hydroxyethyl methacrylate and said second monomer is n-hexyl methacrylate, and further wherein the ratio of the first monomer and the second monomer is 1:1; and
    a bioactive agent.

2. The implantable medical device of claim 1, wherein said bioactive agent is selected from the group consisting of anti-proliferatives, estrogens, chaperone inhibitors, protease inhibitors, protein-tyrosine kinase inhibitors, leptomycin B, peroxisome proliferator-activated receptor gamma ligands (PPAR γ), hypothemycin, nitric oxide, bisphosphonates, epidermal growth factor inhibitors, antibodies, proteasome inhibitors, antibiotics, anti-sense nucleotides, and transforming nucleic acids.

3. The implantable medical device of claim 2, wherein said anti-proliferative is zotarolimus.

4. The implantable medical device of claim 1, wherein said implantable medical device is a vascular stent.

5. A vascular stent comprising:
    a biocompatible polymer comprising monomers consisting of a first monomer and a second monomer wherein said first monomer is 2-hydroxyethyl methacrylate and said second monomer is n-hexylmethacrylate, and further wherein the ratio of the first monomer and the second monomer is 1:1; and
    an anti-proliferative bioactive agent.

6. A vascular stent comprising:
    a biocompatible polymer comprising monomers consisting of 2-hydroxyethyl methacrylate and n-hexyl methacrylate, wherein the ratio of 2-hydroxyethyl methacrylate and n-hexylmethacrylate is 1:1; and
    a bioactive agent.

* * * * *